United States Patent [19]

Weisz

[11] 3,996,350

[45] Dec. 7, 1976

[54] METHODS AND COMPOSITIONS FOR ALLEVIATING FUNGUS INFECTIONS OF THE SKIN

[76] Inventor: Geraldine Fay Weisz, 2240 Harmain Road, Pittsburgh, Pa. 15235

[22] Filed: July 24, 1975

[21] Appl. No.: 598,635

Related U.S. Application Data

[63] Continuation-in-part of Ser. No. 537,969, Jan. 2, 1975.

[52] U.S. Cl. ............................................. 424/151
[51] Int. Cl.$^2$ ...................................... A61K 33/16
[58] Field of Search ................................... 424/151

[56] References Cited

UNITED STATES PATENTS

| | | | |
|---|---|---|---|
| 500,549 | 7/1893 | Baekeland | 424/151 |
| 1,732,240 | 10/1929 | Menzies | 424/151 |
| 2,091,075 | 8/1937 | Landers | 424/151 |
| 2,095,464 | 10/1937 | Chesnutt, Jr. | 424/151 |
| 2,709,665 | 5/1955 | Campbell et al. | 424/151 |
| 3,883,661 | 5/1975 | Young | 424/320 |

OTHER PUBLICATIONS

Hopponen, Handbook of Non-Prescription Drugs, 1973 Edition, pp. 155–160, Published by the American Pharmaceutical Association.

*Primary Examiner*—Norman A. Drezin
*Attorney, Agent, or Firm*—Buell, Blenko & Ziesenheim

[57] ABSTRACT

A method and composition for treatment of bacterial and fungus infections of the skin such as acne and athlete's foot is provided wherein an aqueous solution of a water soluble fluoride and a surface active agent is applied to a skin area affected.

5 Claims, No Drawings

METHODS AND COMPOSITIONS FOR ALLEVIATING FUNGUS INFECTIONS OF THE SKIN

This application is a continuation-in-part of my copending application Ser. No. 537,969, filed Jan. 2, 1975.

This invention relates to methods and compositions for treatment of acne and bacterial and fungus infections of the skin and particularly to methods and compositions for treatment of the skin disorder known as acne vulgaris and fungus infections of the skin such as, for example, Tinea pedis (athlete's foot).

The physical and psychological effects of acne on young persons are very well known. Moreover, there is no skin disorder which is easier to diagnose than acne, however, there are few skin disorders that are more persistent and more difficult to cure.

Acne vulgaris is a chronic inflammatory disease of the sebaceous glands and is characterized by the formation of comedones, appules and pustules of the face, neck and back. It has been suggested that acne vulgaris is a result of physiological activation of the sebaceous system, resulting from changes in the endocrine balance coincident with adolescence. Whatever the causitive process may be, the results on adolescents is well known. Inferiority complexes, backwardness and timidity in adults are frequently traced to a neglected or untreated acne of long duration in the adolescent years. Serious disfigurement of the facial skin may result from the acne or its improper treatment. While mild acne is almost normal with puberty, it is a skin disease which cannot be ignored not only because of the unsightly skin condition which characterizes it but also because of the frequent scarring and long term psychological effects which it induces.

There have been many treatments proposed and used for dealing with acne vulgaris but in most cases they are too involved or too expensive or require an extraordinary degree of self-discipline in the patient. For example, there have been systemic treatments proposed which depend upon the patient following a strict diet which includes the discontinuance of the use of chocolate, iodized salt, white bread, greasy and sweet foods and very rich foods. Since this is a disease primarily of adolescence and since the diet of most adolescents is very high in these very things which are proscribed, the dietary control approach is most unsatisfactory. Vaccine therapy has been suggested and in some cases is of great benefit, but it requires treatment by a physician and is not always effective. Roentgen ray treatment when properly administered is of value in many cases but it can be used only on older children and must be used with extreme care. Again, this treatment requires attendance of a physician and is expensive. Moreover, people are reluctant and resistant to use this because of the danger of overexposure. Ultraviolet light has been suggested as a treatment and while it does appear to be of symptomatic benefit, it is not curative of the disease. In addition, vast numbers of ointments, lotions, powders and the like have been proposed for the treatment of acne.

In the case of superficial fungus infections of the skin or its appendages, the dermatophytes usually invade only the dead tissue of the body surface (stratum corneum, nails, hair) but they may invade living cells in patients with systemic disease such as diabetes, rheumatoid arthritis and lymphoma. Microsporium, Trichophyton, and Epidermophyton are the genera principally involved. Some fungi produce only mild and non-inflammatory reactions. In some cases, the course of the infection consists of gradual extension of scaling, slightly raised border, and intermittent remissions and excerbations. The causative organisms may persist indefinitely as in chronic ringworm of the scalp and of the non-hairy skin caused by T. rubum. In other cases, there may be a sudden vesicular and bulbous flare-up (e.g., ringworm of the feet or a keroin in ringworm of the scalp). The fungi are cast off and complete cure or remission may result.

Since clinically it is difficult to differentiate infection caused by related fungi, it is convenient to discuss cutaneous fungus infection according to the involved sites. Confirmation of the diagnosis is obtained when pathogenic fungus is demonstrated in scrapings of the superficial cutaneous. It is given either by direct microscopic examination or by culture.

Since the most common and best known of these fungi is that generally known as athlete's foot (Tinea pedis), we will confine the discussion to just this disease. Athlete's foot, or dermatophytosis is caused by a fungus, a form of plant life which grows on the dead cells of the feet and thrives on warmth and dampness. It causes itching, burning and often blisters, usually between the toes. In addition to discomfort, it provides sites for more serious infections. It is a contagious infection. Its spread has been traditionally associated with the floors of any place where people customarily go barefoot whether it be the family bathroom or locker room at the local golf club, public swimming pool or school gymnasium. It is characterized by the presence of vesicles, those tiny fluid filled water blisters.

There are two forms of athlete's foot—acute and chronic. Acute takes shape quickly heralded by the sudden itching, burning or what victims describe as a "prickly sensation." The skin becomes scaly and cracks as the attack develops. Fluid oozes from the vesicles. The itching, burning almost intensifies when the vesicles are scratched, massaged roughly or otherwise disturbed.

The chronic condition occurs after the initial acute attack has run its course or it may make its first appearance without the acute stage. The crack is usually red and shiny and is surrounded with loosely clinging dead skin. The vesicles soon join the infection with inflammation spreading. They cause the skin to crack, flake and peel in patches. Itching, burning is present from time to time. In the chronic, the fungi may be dormant for long periods. It may be seasonal and it is just apt to flare up in cool weather. The acute is far likely to make its appearance in warm weather.

In the treatment of athlete's foot, as in other of the fungus infections, the first step is practice of good hygiene. Interdigital spaces must be dried after bathing and macerated skin rubbed away. Routine use of a bland, drying and dusting powder may help.

The second step in the treatment is the use of a medication that will kill the fungi. A third step is to set up a regimen of foot care over a period of time to be certain that the fungi do not reappear and reinfect the area.

The fungi breeding and spreading as they do, hiding in the cracked and peeling skin, and clustering even in the scratches on toenails will always be too great in number and to well entrenched for the medication to handle by itself. But in combination, the medication and the program can effectively hold future attacks at bay and can, in time, see the foot completely healed.

I have discovered a treatment and composition which does eliminate acne vulgaris if not complicated by other physical problems. This same treatment is applicable to fungus infections of the skin such as athlete's foot.

The treatment of this infection comprises applying at regular intervals to the affected skin areas a composition consisting essentially of a water soluble fluoride, preferably sodium fluoride, and a surface active wetting agent in aqueous solution. Preferably the composition is used in a concentration such that the fluoride is present in an amount on the order of 1 grain per ounce of solution or approximately 130 grains of fluoride per gallon of solution.

I have found by clinical tests conducted over an extended period and involving more than 100 adolescents between the ages of 14 and 18 that acne vulgaris can effectively be controlled by regular treatment according to this invention. I have found that if treatment is stopped, the acne reappears on the patient but upon resumption of treatment the acne again disappears. The only instance, in my experience with the clinical tests mentioned above, in which the acne was not cured by my treatment was a 14-year-old girl who, in addition to acne problems, had a complicated menstrual disturbance.

I have similarly found that superficial fungus infections of the skin such as athlete's foot can be similarly controlled by regular treatment. The treatment can be applied by shampoos, lotions, ointments, soaps or simply by solutions of the active ingredients herein claimed.

Although I have referred specifically to the use of sodium fluoride, it should be evident that other soluble fluorides, such as stannous fluoride, potassium fluoride, etc., may be employed, provided they are in equivalent or substantially equivalent concentration in water solution.

The wetting or surface active agent constitutes a minor proportion of the composition. As such, there may be employed any of the well-known wetting agents, provided the one selected does not have any substantial effect in the direction of inactivating the fluoride. Preferably, there is employed a powdered form of wetting agent, such as one of the compounds produced and marketed by American Cyanamid and Chemical Corporation, under the trade names of Aerosol AY (diamyl sodium sulfosuccinate), Aerosol IB (dibutyl sodium sulfosuccinate), and Aerosol OS (isopropylnaphthalene sodium sulfonate).

In any event, as above indicated, the surface active agent employed is one which will not react with or otherwise inactivate the soluble fluoride in the concentrations in which the surface active agent would be present when the mix is dissolved in the stated amount of water.

I have discovered, however, that anionic surfactants provide a synergistic effect in addition to the usual wetting effect and are preferred in the practice of this invention.

In general, a dry powder mix suitable for use in accordance with my invention may be composed of the following ingredients in substantially the proportions indicated:

|  | Parts (by weight) |
| --- | --- |
| Sodium fluoride | 115 |
| Wetting agent | 0.1 |
| Sodium chloride | up to 20 |

Sodium chloride need not be present, however, I have found that its presence appears to provide a marked enhancement or synergistic effect with the fluoride when added in amounts indicated above.

A dry mix of the composition set forth above has been demonstrated to be effective when employed in aqueous solution in the concentration herein set forth, viz., such as will provide approximately one grain of the fluoride per ounce of solution. It will be understood, however, that various changes may be made in the composition without departing from the scope of the invention. Thus, as already indicated, other water soluble fluorides, such as stannous fluoride or potassium fluoride may be employed in lieu of the sodium fluoride; likewise other wetting agents, as well as scenting agents may be employed. The proportion of the wetting agent employed may vary, depending primarily upon its surface active properties and upon the particular fluoride employed and the nature of the tap water with which the dry powder mix is to be used for preparing the wash solution.

In a preferred and specific embodiment of the invention, a dry powder mix in conformity with the above-stated general formula may be compounded and packaged in individual envelopes or other suitable containers, each containing the fluoride and other ingredients in amounts as follows:

| Sodium fluoride | grains | 288 |
| --- | --- | --- |
| Aerosol AY (wetting agent) | grains | ¼ |
| Sodium chloride | grains | 56 |
| Scenting agent | minims | 15 |

If desired, appropriate amounts of a suitable dye may also be added as coloring.

With envelopes containing the fluoride and other ingredients in amounts above stated, the user would be instructed, preferably by imprinting suitable directions on each envelope, to dissolve the contents thereof in one quart of distilled or pre-boiled water, and to use one tablespoonful of this solution in one-half glass of water as a wash solution, after first cleansing the face and rinsing all cleansing material from the face or other skin area being treated. The patient is also instructed to use the wash both in the morning and before retiring, by patting the wash onto the affected surface.

It will be seen that when the above-stated contents of an envelope of the dry mix are dissolved and diluted as indicated, the concentration of sodium fluoride in the final solution employed as the wash will represent about 135 grains of sodium fluoride per gallon of water, or fractionally more than one grain per ounce, and hence about 3 to 4 grains per use.

If desired, the composition of my invention may be furnished for use in the form of compressed but readily disintegratable type of tablets, each containing three grains of fluoride and proportional amounts of wetting agent and other ingredients, so that when dissolved in three to four ounces of water, it will provide a solution of the desired concentration of fluoride for use in accordance herewith.

Also, if desired, the composition may be furnished as a pre-formed solution in water, wherein the concentration of the fluoride is of the order of 135 grains per gallon.

As another alternative form, the wash solution may be packaged in the form of pre-wetted packaged gauze pads. These pads may be used to pat the solution onto the acne affected areas or the fungus infected areas as the case may be.

The foregoing detailed description has been given for purposes of explaining and illustrating the invention. It is accordingly to be understood that the invention is not limited to the detailed information set forth, and that various modifications may be made therein without departing from the scope of the invention as defined by the appended claims.

I claim:

1. The method of alleviating fungus infections of the skin which comprises applying to the skin area affected by the fungus an effective amount of an aqueous solution of a water soluble fluoride and a surface active agent of a character having no substantial effect in inactivating the fluoride, the wetting agent being present in a minor proportion relative to the fluoride, and said fluoride being present in an amount effective to alleviate said fungus infection.

2. The method as claimed in claim 1 wherein the surface active agent is an anionic surfactant.

3. The method as claimed in claim 1 wherein the fluoride is sodium fluoride.

4. The method as claimed in claim 1 wherein water soluble fluoride is present in the aqueous solution at a concentration of about 1 grain per ounce.

5. The method as claimed in claim 1 wherein sodium chloride is added in minor proportion relative to the fluoride.

* * * * *